(12) United States Patent
Schaldach et al.

(10) Patent No.: US 6,805,709 B1
(45) Date of Patent: Oct. 19, 2004

(54) STENT HAVING DISCONTINUOUS COATING IN THE FORM OF COATING ISLANDS

(75) Inventors: Max Schaldach, Erlangen (DE); Curt Kranz, Berlin (DE)

(73) Assignee: Biotronik Mess- und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 0 days.

(21) Appl. No.: 09/695,562

(22) Filed: Oct. 24, 2000

(30) Foreign Application Priority Data

Oct. 26, 1999 (DE) .......................................... 199 51 477

(51) Int. Cl.[7] .................................................. A61F 2/06
(52) U.S. Cl. ..................... 623/1.46; 623/1.34; 623/1.42
(58) Field of Search .............. 623/1.15, 1.46, 623/23.64–23.71, 1.34; 427/2.24, 5, 452, 456, 531

(56) References Cited

U.S. PATENT DOCUMENTS

| | | |
|---|---|---|
| 5,674,276 A | 10/1997 | Andersen |
| 5,843,172 A | 12/1998 | Yan |
| 5,849,206 A * | 12/1998 | Amon et al. ................ 623/1.13 |

FOREIGN PATENT DOCUMENTS

| | | |
|---|---|---|
| DE | 693 17 548 T2 | 3/1998 |
| DE | 198 46 013 A1 | 5/1999 |
| DE | 299 08 768 U1 | 9/1999 |
| DE | 198 28 369 A1 | 12/1999 |
| DE | 199 13 978 A1 | 9/2000 |
| EP | 0 679 372 A2 | 11/1995 |
| EP | 0 689 807 A2 | 1/1996 |
| EP | 0 824 900 A2 | 2/1998 |
| EP | 0 916 317 A1 | 5/1999 |
| EP | 0 923 953 A2 | 6/1999 |
| WO | WO 99/58167 A1 | 11/1999 |

* cited by examiner

Primary Examiner—Corrine McDermott
Assistant Examiner—William H Matthews
(74) Attorney, Agent, or Firm—Hahn Loeser & Parks LLP

(57) ABSTRACT

A stent has a surface with an irregular coating formed on that surface. The irregular coating provides coating islands, especially coating islands that are substantially round. In some embodiments, the coating islands are arranged at a greater spacing in regions involving a greater degree of local stretching of the stent surface upon stretching of the stent than in regions involving a lesser degree of local stretching of the stent surface. In other embodiments, the coating islands are smaller in regions involving a greater degree of local stretching of the stent surface upon stretching of the stent than in regions involving a lesser degree of local stretching of the stent surface.

12 Claims, 1 Drawing Sheet

STENT HAVING DISCONTINUOUS COATING IN THE FORM OF COATING ISLANDS

The invention concerns a stent having a coating.

BACKGROUND OF THE ART

Stents are known from the state of the art in many different forms. Stents are used inter alia in connection with percutaneous transluminal angioplasty (PCTA, Percutaneous Transluminal Balloon Angioplasty) in vascular surgery of the heart. Stents however can also serve to dilate other openings in the body or to keep such openings in a dilated condition. That medical procedure is initially preceded by determining the location of the constriction in a coronary blood vessel. A so-called angioplasty balloon is then moved in the artery which has the constriction, the so-called stenosis, to the location of the stenosis where it is inflated. Due to the radially outwardly directed force of the inflated balloon the constriction is dilated and in the optimum case the original passage cross-section of the previously constricted artery is restored.

Besides successful dilation of the vessel however side-effects can occur, which include local splits in the artery, disintegration effects and projections of plate portions and flakes into the lumen of the artery so that, in spite of the dilation effect, blockage of the vessel can still occur. In addition It is possible that a stenosis can re-occur due to the vessel wall elastically springing back and/or due to the growth of the intima of the vessel. Statistically, that occurs within six months in the case of over 30% of the patients who were treated with PCTA.

Immediately after dilation of the blood vessel and to ensure a relatively smooth inside wall surface for the vessel and to be able to avoid renewed stenosis, stents were developed. Those small tubes serve inter alia in conjunction with PCTA to maintain the vessel flow cross-section which is produced by balloon angioplasty, in order thereby to ensure long-term success with the PCTA procedure.

The success of such so-called stenting also depends inter alia on how quickly blood particles are deposited on the stent when fitted into the vessel. For, the more rapidly blood particles are deposited on the stent surfaces, the more rapidly vessel constrictions recur in the region of the stents, by virtue of such deposits. It is therefore desirable to provide stent surfaces which make it difficult for the blood particles to be deposited on the surface of the stent and thus constrict the flow cross-section of the blood vessel provided with a stent.

In order to prevent deposits of that kind or to at least make it more difficult for them to form, it is therefore known from the state of the art for the surfaces of the stents to be coated with a material which makes it more difficult for blood particles to be deposited on the stent surface, that is to say, on that coating.

When a stent provided with such a coating is now radially expanded in the blood vessel, coatings of that kind are also expanded therewith. In that respect it has been found that those coatings in the state of the art are only capable to a limited extent of following the corresponding expansion of the stent. As a result those stent coatings chip off the stent surface if expansion of the stent and therewith the tension produced in the coating become excessive.

Accordingly, the object of the invention is to avoid the above-indicated disadvantages and to provide a stent of the kind set forth in the opening part of this specification, whose coating does not chip off the stent even upon stretching of the stent.

SUMMARY OF THE INVENTION

In accordance with the invention in a stent of the kind set forth in the opening part of this specification that object is attained in that the coating is formed irregularly on the stent surface.

The advantages of the present invention are in particular that the irregularly formed coating means that the coating can be adapted to meet the prevailing demands in respect of the coating. For, upon expansion of the stent, the fact that the stent is stretched to different degrees in various regions also involves stretching to different degrees of the coating disposed in those regions. Thus, by virtue of the irregularly formed coating, the coating can be thinner at locations where the stent experiences a great degree of stretching, than at locations which involve a lesser degree of stretching of the stent when the stent is inserted into a blood vessel. It is thus possible by virtue of the invention to provide that the coating does not chip or peel off as in its thinner regions it can still follow even extreme local stretching phenomena.

In a further preferred embodiment of the invention the coating is completely removed at at least one location on the surface of the stent. That location is preferably a location involving elevated local stretching of the stent upon expansion of the stent. When the stent has a coating of that kind which is not of a continuous or complete nature therefore there are formed between individual coated regions gaps or joins in which a length compensation effect can occur between the portions of the coating so that the stresses which occur in the continuously closed coating In the state of the art can be reduced. That therefore provides that the coating cannot chip or flake off at that location of extreme local stretching of the stent as the coating is not provided there from the outset. In that respect each gap or join between the individual coated regions delimits a region whose maximum dimensions are afforded by the maximum stretching of the stent which occurs at that location. In adjacent relationship to that free location, that is to say in regions in which the local stretching effect would not result in the coating chipping off, the coating is again present. In that respect the coating may involve a thickness gradient so that the coating becomes uniformly thicker for example from the location at which there is no coating to a location at which no local stretching occurs upon expansion of the stent. That provides for a smooth and gentle surface profile for the coating on the stent.

In a further preferred embodiment of the invention the coating is arranged in a pattern-like or grid-like configuration. In another embodiment of the invention that grid configuration or patterning can also relate to the thickness of the coating. In both cases however this ensures in the patterned configuration that the stent has in a regular fashion thereon coating regions which can withstand even relatively high local stretching effects without chipping off. In this embodiment therefore it is not absolutely necessary to pay attention to precisely locating locations with a high level of local stretching; on the contrary, by means of a coating which is patterned overall in that way it is possible to prevent the coating from chipping off from the outset at any location on the stent. For, in this embodiment, the coating portions which are applied to the stent in a grid-like or pattern configuration are preferably so small that they do not chip off at any event when the stent is subjected to stretching. A stent which is coated in a grid-like or patterned configuration in that way Is therefore inherently immune to the coating chipping off.

In a further preferred embodiment of the present stent coating the coating is arranged in the form of coating islands on the surface of the stent. These coating islands which in a further preferred feature are of a circular configuration best embody the success according to the invention. For, coating islands of that kind can simply be applied in uniform form and at the same time ensure that there is a uniform distribution of the stretch forces acting on the coating in the coating island itself. That avoids stretch effect peaks in the coating itself; thus, in the case of a round coating island of that kind, the stretch loading in respect of the coating island within the coating island is substantially more uniform and regular than in the case of islands which are of an irregular shape.

The invention can also be adapted to various requirements in respect of the stent. Thus, depending on the respective stent structure involved, it is advantageous if all coating islands are of substantially equal size. In this embodiment it is then further preferred if the coating islands in regions involving a greater degree of local stretching of the stent surface upon stretching of the stent are arranged at a greater mutual spacing than in regions involving a lesser degree of local stretching of the stent surface. In this embodiment therefore, with coating islands of equal size, the different degrees of local stretching of the stent are taken into consideration by virtue of different spacings of the coating islands on the surface of the stent.

In other stent structures, it has proven to be advantageous if the mutual spacings of the coating islands are of equal size substantially everywhere on the surface of the stent. In this embodiment, adaptation of the coating to the different degree of stretching of the stent is effected by the coating islands in the regions involving a greater degree of local stretching of the stent surface being smaller than in regions involving a lesser degree of local stretching of the stent surface. In this embodiment therefore adaptation of the coating to varying local stretching of the stent is implemented by way of the size of the coating islands.

In a further particularly preferred embodiment of the present invention the coating is made of biocompatible material. That provides for optimum medical compatibility of the stent.

Further preferred embodiments of the invention are set forth in the appendant claims.

BRIEF DESCRIPTION OF THE DRAWINGS

An embodiment by way of example of the present invention will now be described with reference to the figures, in which.

DETAILED DESCRIPTION OF THE PREFERRED EMBODIMENT

Figure 1:
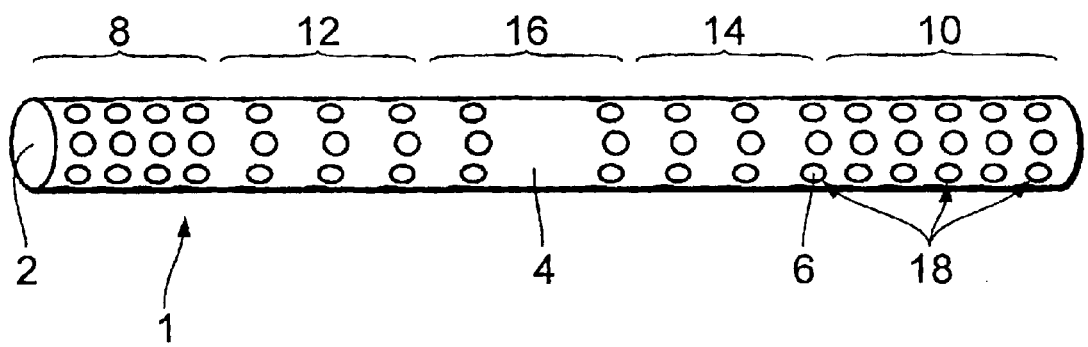
FIG. 1 shows a perspective view of a first embodiment of the present invention.

FIG. 1 shows a portion 1 of a stent according to the invention. The portion 1 comprises a piece of wire 2 of the structure of the stent.

The wire 2 is of a cylindrical configuration and has a surface 4. Disposed on the surface 4 Is a coating 6 which is arranged In a grid-like or patterned configuration.

The wire 2 is incorporated into a stent structure in such a way that, upon stretching (not shown) of the stent, different degrees of local stretching of the wire 2 occur. Thus, the regions 8 and 10 of the wire 2, which are illustrated in the Figure, are stretched only to a slight degree. The regions 12 and 14 of the wire 2 are stretched to a greater degree in comparison, when the stent is stretched overall. The region 16 of the wire 2 is stretched to the greatest degree when the stent is stretched.

Figure 2:
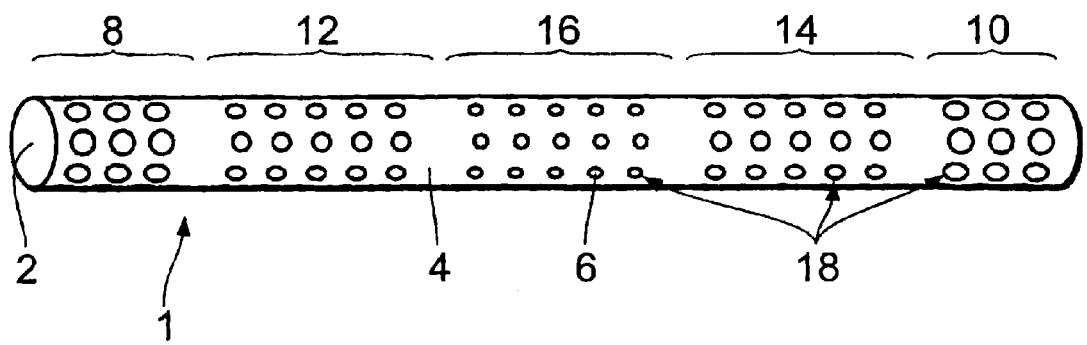
FIG. 2 shows a perspective view of a second embodiment of the present invention.

FIGS. 1 and 2, the coating 6 is applied to the surface 4 of the wire 2 in different densities in accordance with the differing stretching of the regions 8 through 16. That differing density is achieved in that the individual coating islands 18 of the coating 6, which are each of a circular configuration, are arranged at differing spacings relative to each other on the surface 4. Thus, those coating islands 18 of substantially equal size are arranged at a first spacing relative to each other in the regions 8 and 10, while in the regions 12 and 14 they are arranged at a second, greater spacing relative to each other and in the region 16 they are arranged at a third, still greater spacing relative to each other. In that way the coating 16 can also go with the varying degree of stretching of the surface 4, without the coating 6 or the coating islands 18 suffering from spalling from the surface 4 of the wire 2 of the stent upon stretching thereof.

FIG. 2 shows a portion 1 of a stent according to the invention. The portion 1 comprises a piece of wire 2 of the structure of the stent. The wire 2 is of a cylindrical configuration and has a surface 4. Disposed on the surface 4 is a coating 6 which is arranged in a grid-like or patterned configuration. The wire 2 is incorporated into a stent structure in such a way that, upon stretching (not shown) of the stent, different degrees of local stretching of the wire 2 occur. Thus, the regions 8 and 10 of the wire 2, which are illustrated in FIG. 2, are stretched only to a slight degree. The regions 12 and 14 of the wire 2 are stretched to a greater degree in comparison, when the stent is stretched overall. The region 16 of the wire 2 is stretched to the greatest degree when the stent is stretched. The coating 6 is applied to the surface 4 of the wire 2 yielding coating islands of different size in accordance with the differing stretching of the regions 8 through 16. The individual coating islands 18 of the coating 6, which are each of a circular configuration, are arranged at differing spacings relative to each other on the surface 4. Thus, those coating islands 18 of substantially larger size are arranged at a first spacing relative to each other in the regions 8 and 10. In regions 12 and 14 the coating islands 18, which are smaller in size when compared to those in regions 8 and 10, are arranged at a second, greater spacing relative to each other. Lastly, in the region 16 the coating islands 18, which are the smallest in size when compared to the other coating islands 18 of the other regions, are arranged at a third, still greater spacing relative to each other. In that way the coating 16 can also go with the varying degree of stretching of the surface 4, without the coating 6 or the coating islands 18 suffering from spalling from the surface 4 of the wire 2 of the stent upon stretching thereof.

What is claimed is:

1. A stent, comprising:
 a surface with a non-uniform coating formed thereon,
 wherein the non-uniform coating comprises coating islands on the surface,
 wherein the coating islands are substantially round,
 wherein the spacing of the coating islands, prior to radial expansion, is dependent upon the degree of local stretching during radial expansion, and
 wherein the coating islands are arranged at a greater spacing in regions of the stent surface involving a greater degree of local stretching upon stretching of the stent than in regions involving a lesser degree of local stretching of the stent surface.

2. The stent as set forth in claim 1 wherein the coating has a non-uniform thickness.

3. A stent as set forth in claim 2 wherein the coating is completely missing at least one location on the surface of the stent.

4. A stent as set forth in claim 3 wherein the coating is interrupted in a grid-like pattern.

5. The stent as set forth in claim 1 wherein the coating islands are all of substantially the same size.

6. The stent as set forth in claim 1 wherein the coating comprises biocompatible material.

7. A stent, comprising:

a surface with a non-uniform coating formed thereon, wherein the non-uniform coating comprises coating islands on the surface, wherein the coating islands are substantially round, wherein the spacing of the coating islands, prior to radial expansion, is dependent upon the degree of local stretching during radial expansion, and wherein the coating islands are smaller in regions of the stent surface involving a greater degree of local stretching upon stretching of the stent than in regions involving a lesser degree of local stretching of the stent surface.

8. The stent as set forth in claim 7 wherein the coating islands are all of substantially the same size.

9. The stent as set forth in claim 7 wherein the coating has an non-uniform thickness.

10. The stent as set forth in claim 9 wherein the coating is completely missing in at least one location on the surface of the stent.

11. The stent as set forth in claim 10 wherein the coating is interrupted in a patterned configuration.

12. The stent as set forth in claim 7 wherein the coating comprises biocompatible material.

\* \* \* \* \*